United States Patent
Lombardo et al.

(10) Patent No.: US 11,576,665 B2
(45) Date of Patent: Feb. 14, 2023

(54) SOFT ANCHOR MADE FROM SUTURE FILAMENT AND SUTURE TAPE

(71) Applicant: Linvatec Corporation, Largo, FL (US)

(72) Inventors: Giuseppe Lombardo, New Port Richey, FL (US); Andrew K. Kam, Odessa, FL (US); Peter C. Miller, Largo, FL (US); Steven E. Fitts, Largo, FL (US)

(73) Assignee: Linvatec Corporation, Largo, FL (US)

( * ) Notice: Subject to any disclaimer, the term of this patent is extended or adjusted under 35 U.S.C. 154(b) by 312 days.

(21) Appl. No.: 16/894,140

(22) Filed: Jun. 5, 2020

(65) Prior Publication Data

US 2020/0297337 A1    Sep. 24, 2020

Related U.S. Application Data

(60) Division of application No. 15/407,653, filed on Jan. 17, 2017, now Pat. No. 10,687,798, which is a
(Continued)

(51) Int. Cl.
*A61B 17/04* (2006.01)
*A61F 2/08* (2006.01)

(52) U.S. Cl.
CPC .. *A61B 17/0401* (2013.01); *A61B 2017/0403* (2013.01); *A61B 2017/0406* (2013.01);
(Continued)

(58) Field of Classification Search
CPC ............ A61B 17/0401; A61B 17/0487; A61B 2017/0403; A61B 2017/0406;
(Continued)

(56) References Cited

U.S. PATENT DOCUMENTS

| | | |
|---|---|---|
| 4,549,545 A | 10/1985 | Levy |
| 4,741,330 A | 5/1988 | Hayhurst |

(Continued)

FOREIGN PATENT DOCUMENTS

| | | |
|---|---|---|
| EP | 0611551 | 8/1994 |
| WO | WO1999/039644 | 8/1999 |

(Continued)

OTHER PUBLICATIONS

European Patent Office Report, EPO Form 2001, Application No. 12 748 076.2, pp. 1-4, dated Mar. 2, 2017.
(Continued)

*Primary Examiner* — Erich G Herbermann
(74) *Attorney, Agent, or Firm* — Bond, Schoeneck & King, PLLC; Frederick J.M. Price

(57) ABSTRACT

An anchor is provided for placement in or against tissue. The anchor includes a flat fibrous construct having a first end and a second end; and a filament having a first end and a second end passing through the fibrous construct in two locations including a first passing location nearest a first end of the fibrous construct, a second passing location nearest a second end of the fibrous construct, the filament remaining free to slide through the first passing location and the second passing location such that the filament can be removed from the flat fibrous construct from the first end of the fibrous construct and the second end of the fibrous construct. The anchor can be inserted into a bone hole and deployed.

4 Claims, 10 Drawing Sheets

Related U.S. Application Data continuation of application No. 13/466,060, filed on May 7, 2012, now Pat. No. 9,826,971.

(60) Provisional application No. 61/518,519, filed on May 6, 2011.

(52) U.S. Cl.
CPC ..... *A61B 2017/0445* (2013.01); *A61F 2/0811* (2013.01); *A61F 2002/0888* (2013.01)

(58) Field of Classification Search
CPC ....... A61B 2017/0445; A61B 2017/061; A61F 2/0811; A61F 2002/0888
See application file for complete search history.

(56) References Cited

U.S. PATENT DOCUMENTS

| | | |
|---|---|---|
| 5,403,348 A | 4/1995 | Bonutti |
| 5,423,860 A | 6/1995 | Lizardi et al. |
| 5,540,703 A | 7/1996 | Barker, Jr. et al. |
| 5,584,695 A | 12/1996 | Lal Sachdeva et al. |
| 5,989,252 A | 11/1999 | Fumex |
| 6,511,498 B1 | 1/2003 | Fumex |
| 6,544,281 B2 | 4/2003 | Elattrache et al. |
| 6,991,636 B2 | 1/2006 | Rose |
| 7,066,956 B2 | 6/2006 | Gorsek |
| 7,077,863 B2 | 7/2006 | Schmieding |
| 7,118,581 B2 | 10/2006 | Friden |
| 7,306,626 B2 | 12/2007 | Whelan |
| 7,390,329 B2 | 6/2008 | Westra et al. |
| 7,556,640 B2 | 7/2009 | Foerster |
| 7,588,595 B2 | 9/2009 | Miller et al. |
| 7,749,250 B2 | 7/2010 | Stone et al. |
| 7,972,292 B2 | 7/2011 | Behl et al. |
| 7,988,697 B2 | 8/2011 | Miller et al. |
| 8,128,698 B2 | 3/2012 | Bentley et al. |
| 8,172,871 B2 | 5/2012 | Ken |
| 8,298,262 B2 | 10/2012 | Stone et al. |
| 8,303,604 B2 | 11/2012 | Stone et al. |
| 8,361,113 B2 | 1/2013 | Stone et al. |
| 8,409,225 B2 | 4/2013 | Bull et al. |
| 8,425,554 B2 | 4/2013 | Denove et al. |
| 8,449,552 B2 | 5/2013 | Sanders |
| 8,500,809 B2 | 8/2013 | Saliman et al. |
| 8,506,597 B2 | 8/2013 | Kaiser et al. |
| 8,562,647 B2 | 10/2013 | Kaiser et al. |
| 8,579,553 B2 | 11/2013 | Pierce |
| 8,621,961 B2 | 1/2014 | Burch et al. |
| 8,652,172 B2 | 2/2014 | Denham et al. |
| 8,734,491 B2 | 5/2014 | Seavey |
| 8,795,334 B2 * | 8/2014 | Astorino ............ A61B 17/0469 606/228 |
| 8,828,053 B2 | 9/2014 | Sengun et al. |
| 8,876,900 B2 | 11/2014 | Guederian et al. |
| 8,888,795 B2 | 11/2014 | Chu |
| 8,888,848 B2 | 11/2014 | Saliman et al. |
| 8,951,285 B2 | 2/2015 | Sugimoto et al. |
| 9,078,651 B2 | 7/2015 | Astorino et al. |
| 9,138,223 B2 | 9/2015 | Jolly et al. |
| 9,173,645 B2 | 11/2015 | Overes et al. |
| 9,204,874 B2 | 12/2015 | Denove et al. |
| 9,370,352 B2 | 6/2016 | Astorino et al. |
| 9,445,804 B2 | 9/2016 | Paulos |
| 9,538,998 B2 | 1/2017 | Stone et al. |
| 9,549,730 B2 | 1/2017 | Oba et al. |
| 9,603,591 B2 | 3/2017 | Denham et al. |
| 9,788,826 B2 | 10/2017 | Mccartney |
| 9,795,398 B2 | 10/2017 | Steiner et al. |
| 9,800,027 B1 | 10/2017 | Pierce |
| 9,801,719 B2 | 10/2017 | Miraki |
| 9,826,971 B2 | 11/2017 | Lombardo et al. |
| 9,848,868 B2 | 12/2017 | Saliman |
| 9,913,638 B2 | 3/2018 | Saliman et al. |
| 9,918,711 B2 | 3/2018 | Seavey |
| 10,136,886 B2 | 11/2018 | Norton et al. |
| 10,143,469 B2 | 12/2018 | Denove et al. |
| 10,631,844 B2 | 4/2020 | Astorino et al. |
| 2004/0243135 A1 | 12/2004 | Koseki |
| 2006/0074422 A1 | 4/2006 | Story et al. |
| 2007/0156174 A1 | 7/2007 | Kaiser et al. |
| 2007/0276395 A1 | 11/2007 | Burn |
| 2008/0255613 A1 * | 10/2008 | Kaiser ............. A61B 17/06166 606/232 |
| 2009/0062850 A1 | 3/2009 | Ken |
| 2009/0076547 A1 | 3/2009 | Sugimoto et al. |
| 2009/0171360 A1 | 7/2009 | Whelan |
| 2011/0087248 A1 | 4/2011 | Steffen |
| 2011/0238071 A1 | 9/2011 | Fernandez-Scoma |
| 2012/0003057 A1 | 1/2012 | Leyba |
| 2012/0071878 A1 | 3/2012 | Cowin |
| 2012/0197395 A1 | 8/2012 | Berg |
| 2012/0197396 A1 | 8/2012 | Berg |
| 2013/0218273 A1 | 8/2013 | Bull et al. |
| 2014/0330307 A1 | 11/2014 | Steffen |
| 2015/0133941 A1 | 5/2015 | Saylor et al. |
| 2018/0049755 A1 | 2/2018 | Laviano et al. |

FOREIGN PATENT DOCUMENTS

| | | |
|---|---|---|
| WO | WO2007/005394 | 1/2007 |
| WO | WO2009/029914 | 3/2009 |

OTHER PUBLICATIONS

Ronald Glousman, M.D. and Nicholas Sgaglione, M.D., Labral Repair, JuggerKnot Soft Anchor brochure, 2010, 2011, 12 pages.

* cited by examiner

SOFT ANCHOR MADE FROM SUTURE FILAMENT AND SUTURE TAPE

CROSS-REFERENCE TO RELATED APPLICATIONS

This application is a divisional of U.S. Non-Provisional patent application Ser. No. 15/407,653 filed Jan. 17, 2017, now U.S. patent Ser. No. 10/687,798 issued on Jun. 23, 2020, which is a continuation of and claims the benefit of priority from U.S. Non-Provisional patent application Ser. No. 13/466,060 filed May 7, 2012, now U.S. Pat. No. 9,826,971 issued on Nov. 28, 2017 which claims the benefit of priority from U.S. Provisional Patent Application Ser. No. 61/518,519, entitled "Suture anchor made from suture filament and suture tape", filed on May 6, 2011. The contents of the above-identified applications are incorporated herein by reference in their respective entireties.

FIELD OF THE INVENTION

The present invention is related to a suture anchor made (i) entirely of braided or monofilament suture, or (ii) entirely of braided or monofilament suture tape and suture tape.

BACKGROUND OF THE INVENTION

Anchors are commonly employed during surgical procedures to provide a reliable attachment location for sutures in or against a substrate, those attached sutures then being used to capture and retain other objects, such as soft tissue. As such, the suture anchor plays an important role in attaching objects, such as soft tissue to a substrate. The substrate may be bony tissue or soft tissue. In the case of bony tissue, suture anchors are generally inserted into a pre-formed hole in the bone, so that suture extends out of the hole from the anchor. In the case of soft tissue, suture anchors generally are placed on a side of the soft tissue such that suture extends through a hole in the tissue to extend beyond the soft tissue on a side opposite the anchor.

Commonly, such suture anchors contain at least one ridged member which deforms to create an interference fit with a substrate, the interference fit creating a retention capacity of the anchor. Other suture anchors contain some external feature, such as barbs or screw threads, which interacts with the substrate, through piercing, cutting and/or deforming the substrate, to create a retention capacity. Other anchors include multiple features, such as deployable barbs, to create retention capacity.

Soft suture anchors have also been developed, such as the Biomet JuggerKnot™ (a trademark of Biomet Corporation), which utilizes a stiff braided line, which appears to function as a barb against the side of a hole in a substrate.

Many factors have a direct effect on the actual retention capacity achieved by any suture anchor. For example, the quality of tissue, bony or soft, may increase or decrease the retention capacity by a large degree depending on the design of a particular suture anchor. Similarly, the quality of installation affects the retention capacity. As evidenced by the large number of suture anchors on the market, some suture anchors perform in certain circumstances while other anchors perform better in other circumstances.

In light of the forgoing, there continues to be a need for a suture anchor that can provide a relatively more reliable retention capacity in a variety of substrates and when installed under a variety of complex conditions.

SUMMARY OF THE INVENTION

In accordance with various embodiments of the present invention, a soft anchor is described that can reliably provide an increased diameter in a deployed condition for the creation of retention capacity. Further in accordance with various embodiments of the present invention a method of manufacturing is provided for the creation of such soft suture anchors.

In accordance with one embodiment of the present invention an anchor is provided for placement in or against tissue. The anchor comprises a fibrous construct and at least a first filament. Each filament passes through the construct in at least three passing locations comprising a first passing location nearest a first end of said construct, a last passing location nearest a second end of said construct, and at least one intermediate passing location between said first passing location and said last passing location. In an undeployed state, each filament extends a first length between the first passing location and the last passing location. In a deployed state, each filament extends a second length between the first passing location and said last passing location. The second length is shorter than said first length.

In accordance with one embodiment of the present invention, the fibrous construct is a ribbon having a longitudinal axis extending between the first end and the second end, a length along said longitudinal axis, a mattress thickness and a width.

In accordance with embodiments of the present invention, the passing locations are arranged along or parallel to the longitudinal axis.

In accordance with another embodiment of the present invention, the locations are arranged in a staggered fashion crossing said longitudinal axis.

In accordance with embodiments of the present invention the anchor further comprises a second filament.

In accordance with embodiments of the present invention the first filament comprises a slip knot engaging said second filament near said first end of said construct. Further, the second filament comprises a slip knot engaging the first filament near the second end of said construct. Applying tension to a standing end of the first filament and a standing end of the second filament causes a transition from the undeployed state to the deployed state.

In accordance with embodiments of the present invention the fibrous construct is selected from a group consisting of a woven fabric, an unwoven fabric, a braid, and a knitted fabric.

In accordance with one embodiment of the present invention the fibrous construct is cylindrical having a longitudinal axis, a length along said longitudinal axis, and a diameter about said longitudinal axis.

In accordance with one embodiment of the present invention at least one of said passing locations is aligned with a plane different from a plane of another of said passing locations.

In accordance with the embodiments of the present invention a pleat is formed between adjacent of the passing locations in the deployed state.

In accordance with embodiments of the present invention and in said deployed state, said fibrous construct is larger in at least one direction than said fibrous construct in said undeployed state.

In accordance with the present invention a method is provided for deploying an anchor. The method comprises providing a fibrous construct and providing at least a first filament. Each filament passes through said construct in at least three passing locations comprising a first passing location nearest a first end of the construct, a last passing location nearest a second end of the construct, and at least one intermediate passing location between the first passing location and the last passing location. The method further comprises preparing a hole and passing the fibrous construct into said hole. The construct is in an undeployed state where each filament extends a first length between the first passing location and the last passing location. The method further comprises tensioning each filament. After tensioning, each filament extends a second length between the first passing location and the last passing location. The second length is shorter than the first length such that the fibrous construct is changed to a deployed shape.

In accordance with embodiments of the present invention the method further comprises providing a second element with a slip knot capturing said first element near said second end of said construct. The method further comprises providing the first filament with a slip knot capturing said second filament near said first end of said construct.

In accordance with embodiments of the present invention the method further comprises looping a material to be anchored through a U shaped loop formed by construct. The method further comprises passing working ends of each filament through said hole, and pulling the construct and a portion of the material through and out of the hole with said working ends. The tensioning step comprises pulling on the standing ends from one end of said hole and said working ends from another end said hole.

In accordance with another embodiment, an anchor for placement in or against tissue is provided. The anchor can include, but is not limited to, a flat fibrous construct having a first end and a second end; and a filament having a first end and a second end passing through the fibrous construct in two locations including a first passing location nearest a first end of the fibrous construct, a second passing location nearest a second end of the fibrous construct, the filament remaining free to slide through the first passing location and the second passing location such that the filament can be removed from the flat fibrous construct from the first end of the fibrous construct and the second end of the fibrous construct.

In accordance with an embodiment, the flat fibrous construct includes a lumen and is tubular.

In accordance with an embodiment, the anchor includes a deployed state in which the filament forms a semi-u-shape construct with an interior surface forming an interior space within a bone hole; and the first end and the second end of the flat fibrous construct is positioned within the interior space.

In accordance with an embodiment, the thickness of the flat fibrous construct is greater in the deployed state as compared to the thickness of the flat fibrous construct in an un-deployed state.

In accordance with an embodiment, the filament having a longitudinal axis, the flat fibrous construct including a first state in which the flat fibrous construct is uncompressed and extends along the longitudinal axis of the filament; and a second state in which the flat fibrous construct is compressed and expanded in a direction perpendicular to longitudinal axis of the filament.

In accordance with an embodiment, the anchor further includes an intermediate location at which the filament passes through the flat fibrous construct.

In accordance with further embodiment, an anchor system is provided. The anchor system includes, but is not limited to, an anchor including a flat fibrous construct having a first end and a second end; and a filament having a first end and a second end passing through the fibrous construct in two locations including a first passing location nearest a first end of the fibrous construct, a second passing location nearest a second end of the fibrous construct, the filament remaining free to slide through the first passing location and the second passing location such that the filament can be removed from the flat fibrous construct from the first end of the fibrous construct and the second end of the fibrous construct; and an installation device including an end around which the filament is positioned, the flat fibrous construct also being positioned around the end of the installation device between the end of the installation device and the filament.

In accordance with an embodiment, the end of the installation device comprising a fork around which the filament and the flat fibrous construct are positioned with the flat fibrous construct being positioned around the fork between the fork and the filament.

In accordance with an embodiment, the first end and the second end of the flat fibrous construct extending along opposite sides of the installation device, wherein a distance from the filament positioned around the fork to the first end of the fibrous construct is between 7.5 mm to 15 mm.

In accordance with an embodiment, the first end and the second end of the flat fibrous construct extending along opposite sides of the installation device, wherein a distance from a distal end of the fork to the first end of the fibrous construct is between 8.5 mm to 17 mm.

In accordance with an embodiment, the flat fibrous construct comprises a lumen and is tubular.

In accordance with an embodiment, the anchor comprises a deployed state in which the filament forms a semi-u-shape construct with an interior surface forming an interior space within a bone hole; and the first end and the second end of the flat fibrous construct is positioned within the interior space.

In accordance with an embodiment, the thickness of the flat fibrous construct is greater in the deployed state as compared to the thickness of the flat fibrous construct in an un-deployed state.

In accordance with an embodiment, the filament having a longitudinal axis, the flat fibrous construct including a first state in which the flat fibrous construct is uncompressed and extends along the longitudinal axis of the filament; and a second state in which the flat fibrous construct is compressed and expanded in a direction perpendicular to longitudinal axis of the filament.

In accordance with an embodiment, the anchor further includes an intermediate location at which the filament passes through the flat fibrous construct.

In accordance with an embodiment, a method of anchoring tissue to bone is provided. The method includes the steps of providing an anchor including a flat fibrous construct having a first end and a second end; and a filament having a first end and a second end passing through the fibrous construct in two locations including a first passing location nearest a first end of the fibrous construct, a second passing location nearest a second end of the fibrous construct, the filament remaining free to slide through the first passing location and the second passing location such that the filament can be removed from the flat fibrous construct from the first end of the fibrous construct and the second end of the fibrous construct; inserting the anchor into a hole in a bone; and deploying the anchor into the hole.

In accordance with an embodiment, the flat fibrous construct comprises a lumen and is tubular.

In accordance with an embodiment, the anchor includes a deployed state in which the filament forms a semi-u-shape construct with an interior surface forming an interior space within a bone hole; and the first end and the second end of the flat fibrous construct is positioned within the interior space.

In accordance with an embodiment, the thickness of the flat fibrous construct is greater in the deployed state as compared to the thickness of the flat fibrous construct in an un-deployed state.

In accordance with an embodiment, the filament having a longitudinal axis, the flat fibrous construct including a first state in which the flat fibrous construct is uncompressed and extends along the longitudinal axis of the filament; and a second state in which the flat fibrous construct is compressed and expanded in a direction perpendicular to longitudinal axis of the filament.

BRIEF DESCRIPTION OF THE DRAWINGS

So that the manner in which the above recited features of the present invention can be understood in detail, a more particular description of the invention briefly summarized above may be had by reference to the figures, some of which are illustrated and described in the accompanying appendix. It is to be noted, however, that the appended figures illustrate only typical embodiments of this invention and are therefore not to be considered limiting of its scope, for the invention may admit to other equally effective embodiments. Moreover, the drawings are not necessarily to scale, with emphasis generally being placed upon illustrating the principles of certain embodiments of invention.

Thus, for further understanding of the nature and objects of the invention, references can be made to the following detailed description, read in connection with the specification following below in which.

DETAILED DESCRIPTION OF THE INVENTION

Figure 1:
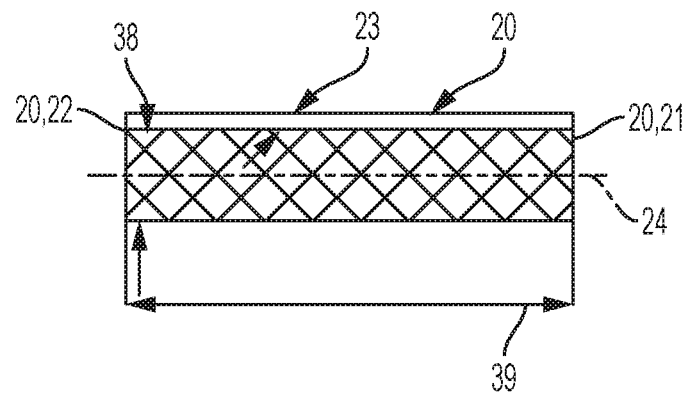
FIG. 1 represents a fibrous construct for use with various embodiments of the present invention.

With reference to FIGS. 1-15, there is provided a soft anchor, variations and embodiments of which are configured so that in a deployed state, the soft anchor enlarges to a predictable, enlarged diameter. This enlarged diameter may be used to laterally displace cancellous tissue forming the sides of a preformed bone hole and to engage the harder cortical layer of the bony tissue. This enlarged diameter may also be used to engage an outer surface of a bony or soft tissue to prevent passage of the enlarged diameter through an adjacent hole in that bony or soft tissue.

Before discussing specific embodiments, it may be helpful to understand that each of the soft anchors discussed herein contain two sections: at least one filament, which is a suture to be anchored; and a fibrous construct, which is to form a portion of the anchor that increases in diameter as part of deployment. Even though it is the fibrous construct that increases in diameter at deployment, it should be understood that the filament also plays a role in the anchor even though the filament may remain free (in some embodiments) to slide in relation to the fibrous construct. The filament helps to position, align and support the fibrous construct, such that if the filament were to be removed from the fibrous construct after deployment of the anchor, the fibrous construct may be free to spill (i.e., release), allowing the fibrous construct to collapse and shrink in size, allowing for easy removal.

In other words, the fibrous construct has two primary functions. First, it becomes a base for the filament to slide within. Second, when compressed and/or pleated during deployment, the fibrous construct becomes more compact in one direction thereby expanding outwardly and increasing its overall diameter to create a retention capacity. This action of having the fibrous construct change in shape to increase its overall diameter is a useful characteristic which may be used advantageously to secure the anchor in a hole or against a bony or soft tissue. It is this combination of the expanding fibrous construct coupled with the filament remaining slidable (in some embodiments) in relation to the fibrous construct that render the present invention ideal for the reattachment of soft tissue to bone or soft tissue to soft tissue where it is desirable to pass sliding knots to secure a repair.

The term 'standing end" is used throughout the following to refer to one or both of the ends of a filament that will ultimately be placed under load by a surgeon during surgery. In relation to at least one embodiment, the term "working end" is used to describe an end of a filament used to create a knot. This is the end that would be pulled to tighten the knot while pulling the standing end may cause to the knot to slide, as in the case of the slip knot described herein.

Filament, as the term is used and described herein, includes braided (i.e., multi-filament) suture and monofilament suture as well as any other metallic or non-metallic filamentary or wire-like material suitable for performing the function of a suture. This material can include both absorbable and non-absorbable materials.

FIGS. 1-6 disclose a first embodiment and a method of deploying the first embodiment.

FIG. 1 shows a fibrous construct 20, which may more commonly be referred to as a suture tape. The fibrous construct 20 has a first end 20, 21 and a second end 20, 22 along with a mattress thickness 23, a width 38 and a length 39 along a longitudinal axis 24. Note that a more specific description of the construction and material of the fibrous construct 20 will follow after the remaining portions of the anchor 1 are described.

Figure 2:
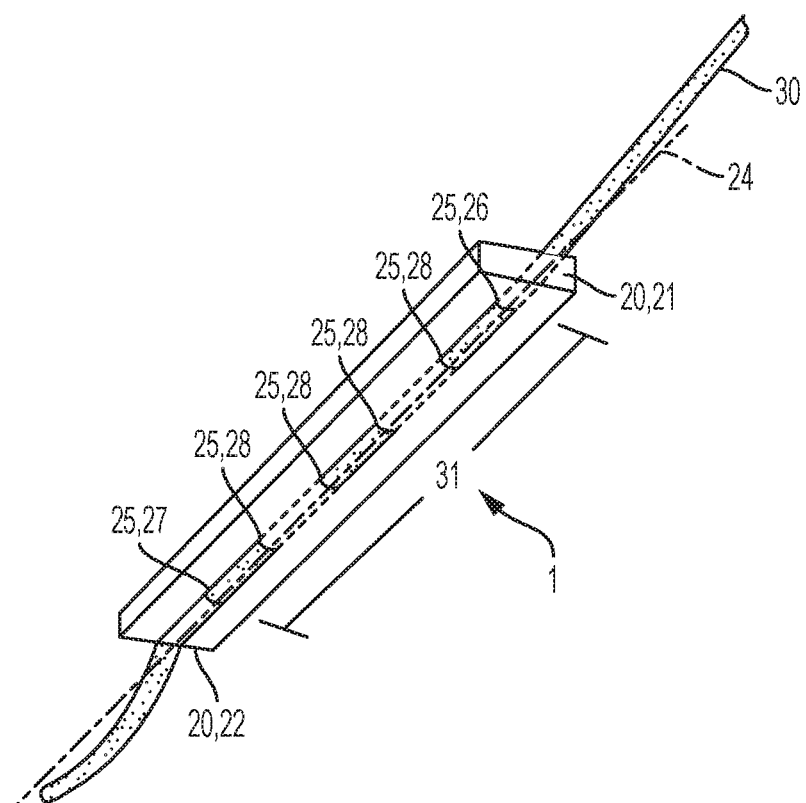
FIG. 2 represents a first embodiment of the present invention.

Referring now to FIG. 2, the anchor 1 includes a filament 30, which is passed through the fibrous construct 20 at passing locations 25. To help explain the function of the anchor 1, it may be helpful to define a first passing location 25, 26, which is a passing location 25 nearest the first end 21 of the fibrous construct 20. Similarly, a last passing location 25, 27, is a passing location 25 nearest the second end 22 of the fibrous construct 20. Each passing location 25 is a location where the filament 30 passes through the mattress thickness 23 of the fibrous construct 20. In the present instance shown in FIG. 2, there are six passing locations 25. For reasons that will become more evident, as few as three passing locations 25 on a particular anchor 1 may function well. Similarly, more passing locations 25 may be provided, but there appears to be a reasonable limit where more passing locations provide no benefit or where additional passing locations actually hurt performance. It has been discovered that each additional passing location increases friction against the filament 30 thus reducing a surgeon's ability to slide the filament 30 in relation to the fibrous construct 20. Therefore, with any material change of the fibrous construct 20, some experimentation is expected to balance ability for the anchor to increase in size upon deployment against ability for the filament 30 to slide in relation to the fibrous construct 20. Lastly on this point, there may be even or odd numbers of passing locations 25.

All of the passing locations 25 in the anchor 1 of FIG. 2 occur along the longitudinal axis 24. Instead, the passing locations 25 may be offset a distance from the longitudinal axis 24 such that they are arranged parallel to the longitudinal axis 24. Similarly, the passing locations may be staggered such that one passing location is on one side of the longitudinal axis 24 while an adjacent passing location 25 is on an opposite side of the longitudinal axis 24.

Figure 6:
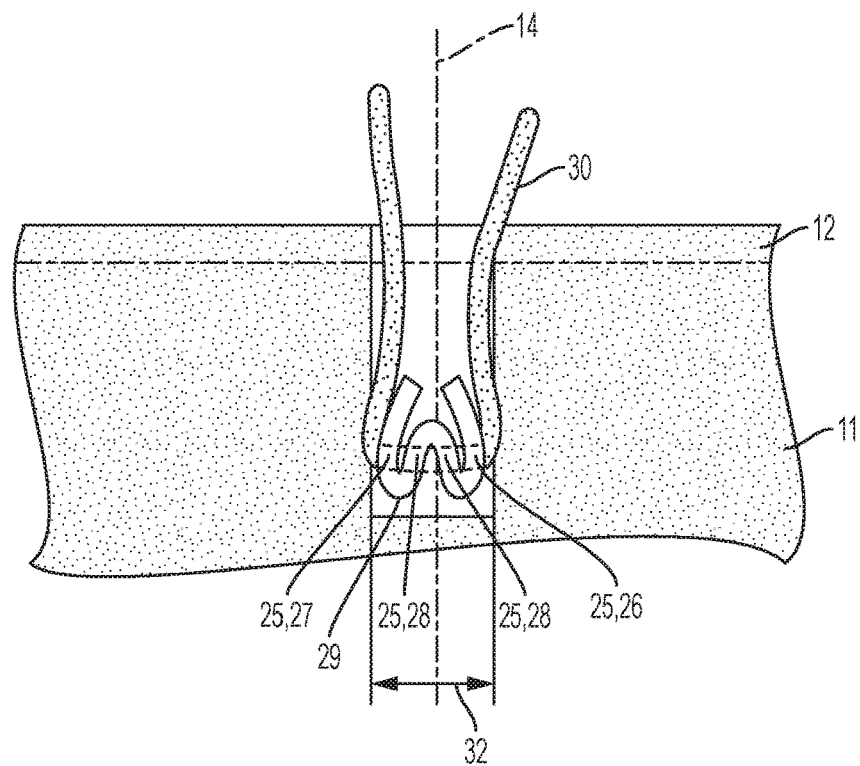
FIG. 6 represents the embodiment of FIG. 4, in a deployed state in accordance with the present invention.

A first distance 31 between the first passing location 25, 26 and the last passing location 25, 27 is an important aspect of FIG. 2 even though its importance will not become evident until the discussion relating to FIG. 6. This first distance 31 is measured in the undeployed or uninstalled state as it is reduced to a second distance 32 (FIG. 6) in the deployed state.

Lastly in relation to FIGS. 1 and 2, a fibrous construct 20 in accordance with the present invention may have a ribbon length of 15-30 mm with a preferred length of 25 mm. The width 38 of the fibrous construct 20 may be 2-4 mm with a preferred width of 3 mm. The mattress thickness 23 was found to vary greatly (due to relative tension or compression) and all were found to work well. Additional passing locations 25 can be added when using a fibrous construct 20 having a relatively thin mattress thickness 23, and vice versa.

Figure 3:
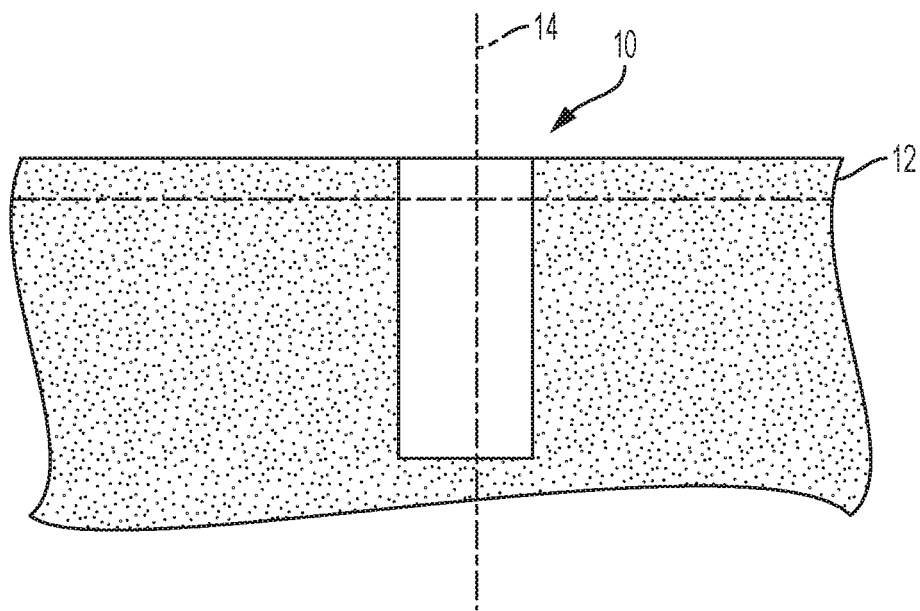
FIG. 3 represents a typical environment for deployment of various embodiments of the present invention.

FIG. 3 is merely a representation of a hole 10 prepared in bone for the anchor 1 to be deployed. In this view, the hole 10 extends along an axis 14 through a cortical layer 12 and into relatively softer cancellous bone 11. This hole 10 may be made using any of the known techniques, such as a drill or punch. It should be understood that the anchor 1 is designed for a particular diameter through the selection of a particular mattress thickness 23, and number of passing locations 25.

Figure 4:
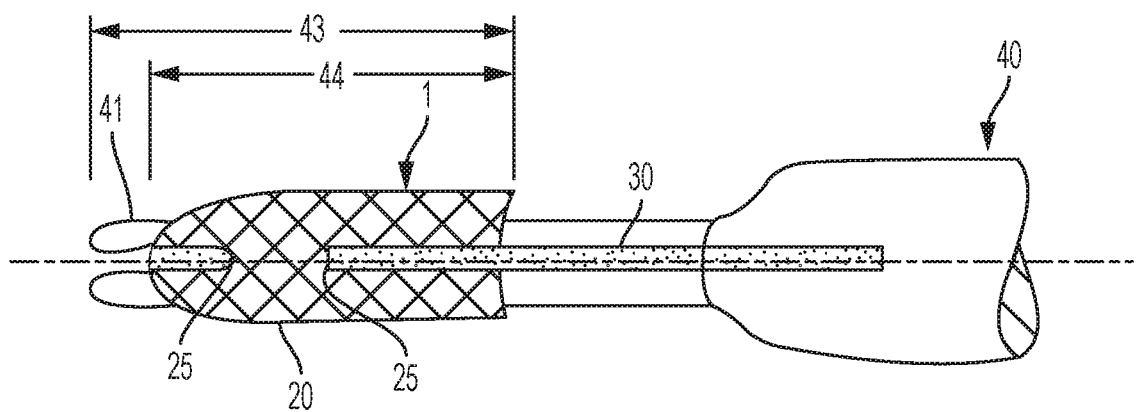
FIG. 4 represents an embodiment of the present invention and an installation device in accordance with the present invention.

Referring now to FIG. 4, the anchor 1 is assembled onto an installation device 40 having a forked end 41. The anchor 1 is arranged on the installation device 40 such that half of the fibrous construct 20 extends along one side of the installation device 40 while the other half extends along a far side of the installation device 40. In each instance, the filament 30 and the fibrous construct 20 are passed through the fork 41. Note that the fibrous construct 20 of FIG. 4 is slightly different variation of the fibrous construct 20 of FIG. 2 in that there are only four passing locations 25, two passing locations 25 visible and two passing locations 25 on the far side.

It has been found that a distance 44 from the filament to an end of the fibrous construct 20 may be from 7.5-15 mm, with 12 mm working especially well. It has also been found that a distance 43 from the distal end of the installation device 40 to an end of the fibrous construct 20 may be from 8.5-17 mm with 15 mm working especially well.

As may be seen on FIG. 4, a distal end portion of the installation device 40 may have a reduced diameter. It has been found that the smallest possible diameter, with strength being a limiting factor, is preferred because the anchor 1 is required to expand an amount to account for the installation device 40 in addition to an amount necessary to displace cancellous bone 11.

Figure 5:
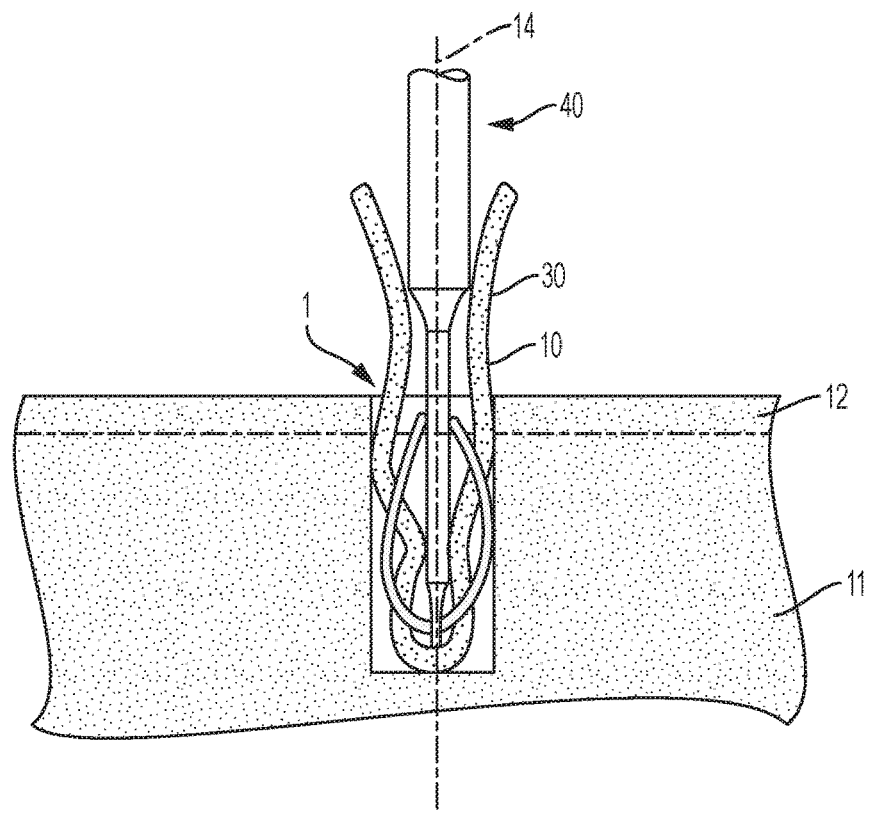
FIG. 5 represents the embodiment of FIG. 4 in the typical environment of FIG. 3 with the anchor in an undeployed state in accordance with the present invention.

Referring now to FIG. 5, the installation device 40 and the anchor 1 are inserted into the hole 10. Note that the relative fit of the anchor 1 in the hole 10 is shown as overly "loose" for the purpose of provided a clear view for the preset description. Ordinarily, the filament 10, fibrous construct 20, and installation device 40 would be tightly pressed into the hole 10, as any excess space would need to be taken up by the expansion of the anchor 1.

As shown in FIG. 5, the filament 30 and the fibrous construct 20 are installed in an elongated fashion along them to pass take on a smallest diameter configuration, referred to herein as a undeployed state or installation state. Again, the depiction in FIG. 5 is loose for the sake of clarity.

Looking now to FIG. 6, deployment occurs as the installation device 40 is removed and the filament 30 is tensioned causing the fibrous construct 20 to grip the wall of the cancellous bone 11 and expand into a deployed state, also referred to herein as the second state. As with FIG. 5, this view is shown loose for clarity in that the filament 30 would likely be much closer to one another.

More importantly, FIG. 6 depicts how the fibrous construct 20 is folded to form pleats 29 between adjacent passing locations 25. This pleating reduces the distance between the first passing location 25, 26 and the second passing location 25, 27, as measured along the filament 30, from the first distance 31 (FIG. 2) to the second distance 32, which is relatively shorter than the first distance 31. These pleats 29 form a stack of the mattress thicknesses 23 (FIG. 1) effectively increasing a diameter (as measure in relation to the axis 14 of the hole 10, causing the anchor 1 to displace cancellous bone 11. This relative increase in size in distance from the axis 14 of the hole 10 creates a retention force of the anchor 1.

As can be understood from FIG. 6, increasing the number of passing locations 25 from the four shown to five, six, seven or more is likely to increase the size of the anchor 1 after deployment and the number of pleats 29 is therefore increased. As mentioned above, a limiting factor is an amount of friction increased by additional passing location 25. It should be understood that a reducing the number of passing locations 25 to three may also function well in certain instances.

In light of the forgoing, it may now be understood that a large variety of contractions and materials will work for the fibrous construct 20. It has been discovered that for each type of construction (i.e. braided, woven, non-woven, or knitted) there is an advantage for using a material that increases in width 38 for every reduction in length 39. This advantage provided for increased diameters for a particular number of pleats 29. On other words, this Poison's ratio of width and/or mattress thickness growth during a reduction in length provides for an increase in deployment size that is additive to the increase due to the pleats.

Further, certain constructions may be found to possess an initial state that is longer on length along the longitudinal access and thus thinner in mattress thickness and width. Such an initial state may help to reduce a diameter of a particular anchor's initial or first state while continuing to result in a large (relatively) deployed or second state.

The material itself may ultra-high molecular weight (UHMW) polyethylene, polyester, or many of the other known implantable materials. More importantly, the material must be able to deform into the shapes discussed further below while remaining capable of retaining a suture from tearing through. In other words, it is acceptable to use a material of lesser strength.

Figure 7:
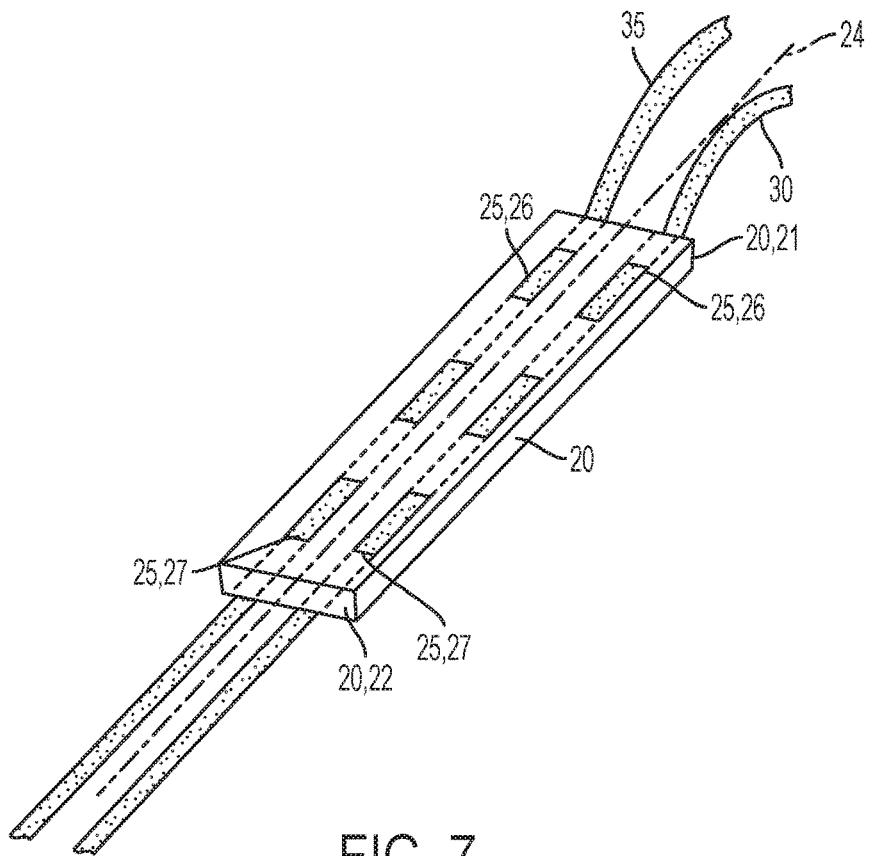
FIG. 7 represents a variation of the embodiment of FIGS. 2 and 4.
Figure 8:
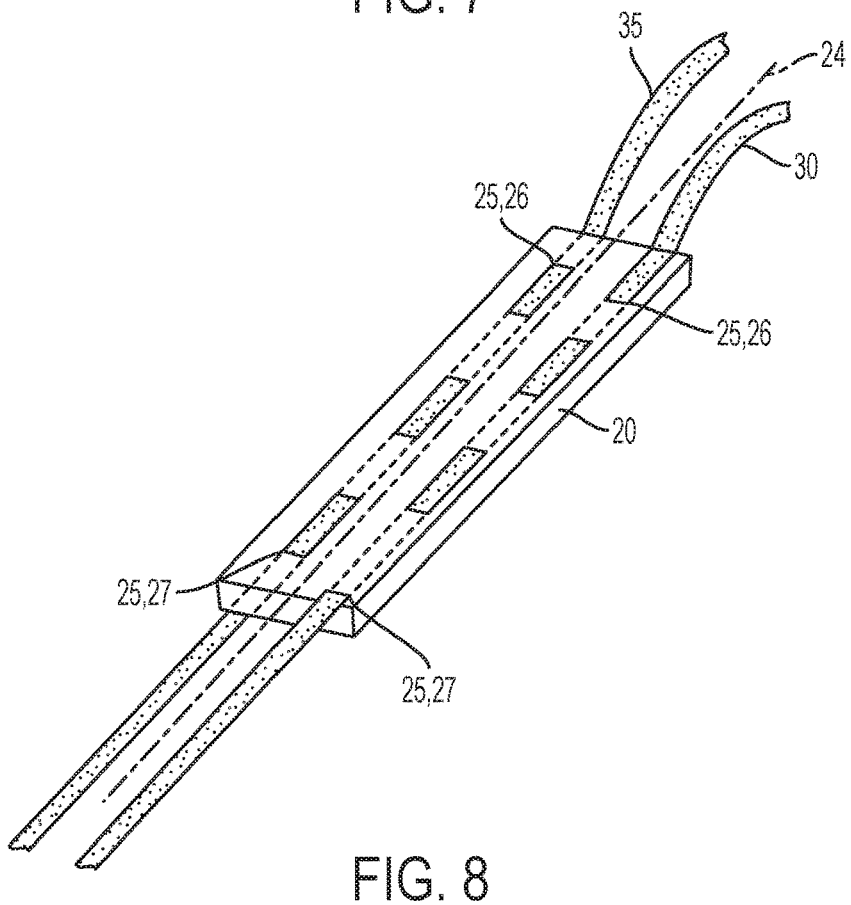
FIG. 8 represents a variation of the embodiment of FIGS. 2 and 4.

FIGS. 7 and 8 show variations of the first embodiment, each of these variations having two filaments 30, 35. In the variation of FIG. 7, the first filament 30 and the second filament 35 have a similar number of and arrangement of passing locations 25. The variation of FIG. 8 includes a similar arrangement where the filament 25 is passing oppositely through a similar number and arrangement of passing locations 25.

With the addition of the second filament 35, it is contemplated that the number of filaments may become confusing, especially in the confines experienced during surgery. This issue is of special concern in light of these anchors 1 because of the additional suture material present. Accordingly, it is envisioned that there be some form of color change at least between the first filament 30 and the second filament 35. Further, it is envisaged to identify each of the free ends of the filaments 30, 35 with different colors. This could be accomplished by having set lengths of particular colors or dying the free ends of the filaments 30, 35.

Figure 9:
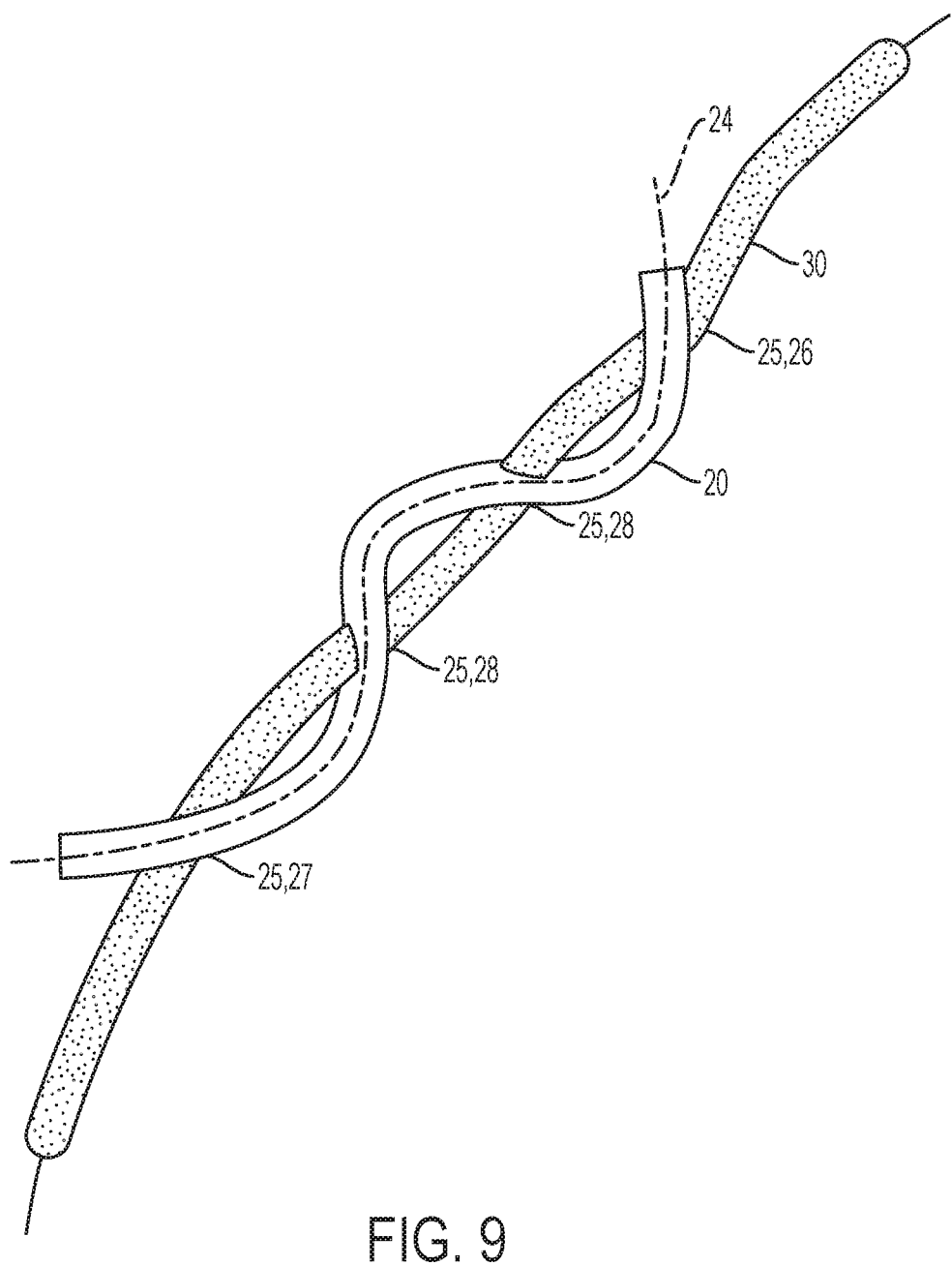
FIG. 9 represents a variation of the embodiment of FIG. 2.

FIG. 9 shows a variation of the first embodiment that is similar is form and function to the anchor 1 of FIGS. 1-6 except the fibrous construct 20 is cylindrical as opposed to a flat tape. Again, this embodiment is similar to the anchor 1 of FIGS. 1-6 in that it is installed in an undeployed state and forms pleats when a distance between the first passing location 25, 26 and the second passing location 25, 27 is reduced during deployment. Note that because of the cylindrical nature of the fibrous construct 20, the filament 30 may be beneficially passed through the fibrous construct 20 in different plane. As shown in FIG. 9, at the first passing location 25, 26 and the last passing location 25, 27, the pane is parallel to the drawing sheet. At each of the two intermediate passing locations 25, 28, the filament 30 is passed through the fibrous construct 20 in a plane perpendicular to the sheet of the page. Accordingly, pleats will still be formed between each of the passing locations 25, but they will likely be formed at differing angles, thus creating expansion in differing directions (but still away from the axis 14 of the hole 10).

Referring now to FIGS. 11-15, a second embodiment is shown. Note that is embodiment is quite similar to the variations of FIGS. 7 and 8 while also remaining quite similar to other variations of the first embodiment. Accordingly, all of the reference numbers remain similar.

The embodiment of FIGS. 11-15 further includes slip knots 42 in each of the filaments 30, 35. In particular, a first slip knot 30, 42 in the first filament 30 is formed near the second end 22 of the fibrous construct 20. This first slip knot 30, 42 captures the second filament 35. A second slip knot 35, 42 is formed in the second filament 25 near the first end 21 of the fibrous construct 20. This second slip knot 35, 42 captures the first filament 30. Otherwise, the construction of the anchor 100 of this embodiment is similar to the earlier embodiments and variations.

Figure 11:
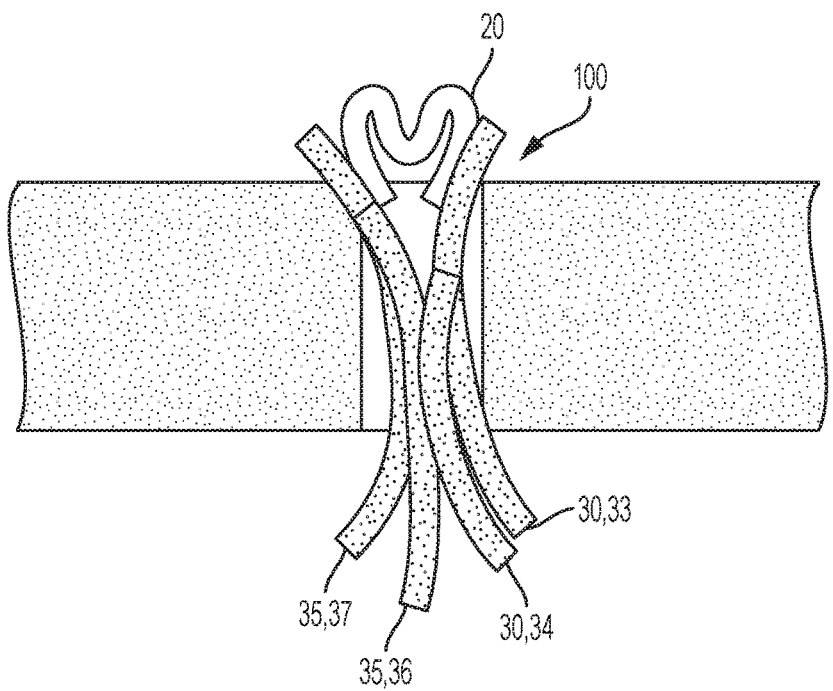
FIG. 11 represents a deployed state of the embodiment of FIG. 10.

As shown in FIG. 11, the addition of the first slip knot 30, 42 and the second slip knot 35, 42 allow for deployment of the fibrous construct 20 and the overall anchor 100 into a deployed state without being confined in a hole. Rather, by pulling the a standing end 33 of the first filament 30 and a standing end 36 of the second filament 35, the knots 42 force the fibrous construct 20 into the deployed state such that is becomes too large to pull back through any hole from which it was originally passed. Once deployed, the standing ends 33, 36, a working end 34 of the first filament 30 and a working end 37 of the second filament 35 may be tensioned. Note that by tensioning the working ends 34, 37, each of the knots 42 will be tightened, helping to lock the filaments 30, 35 in relation to the fibrous construct 20.

Figure 10:
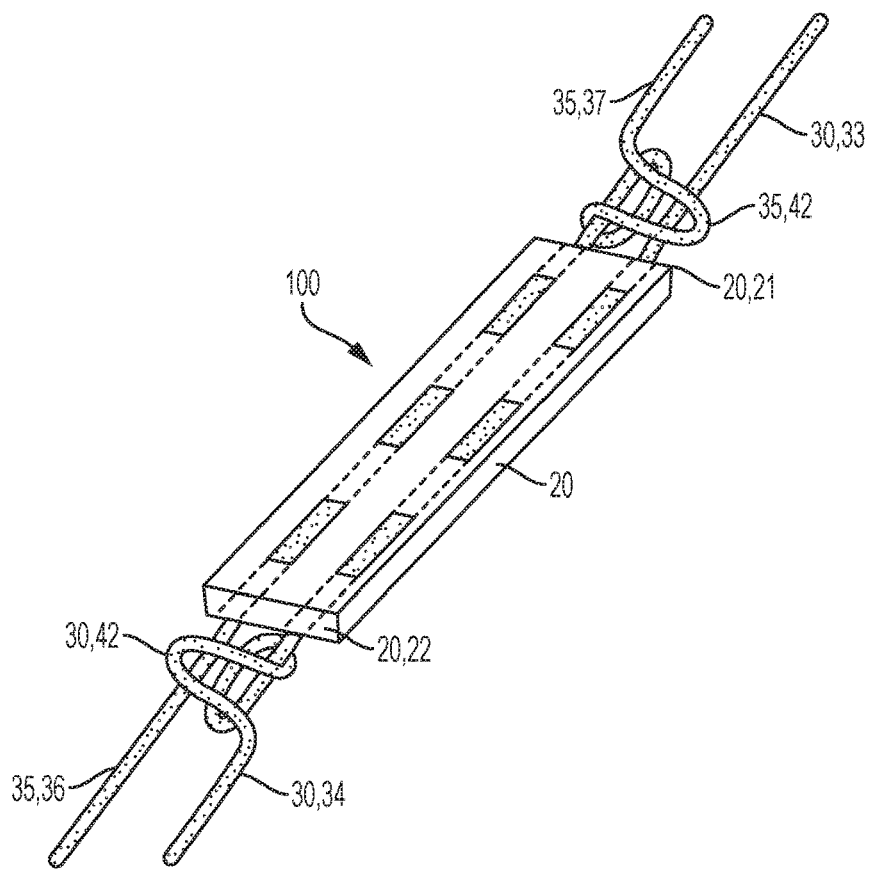
FIG. 10 represents a second embodiment of the present invention.
Figure 12:
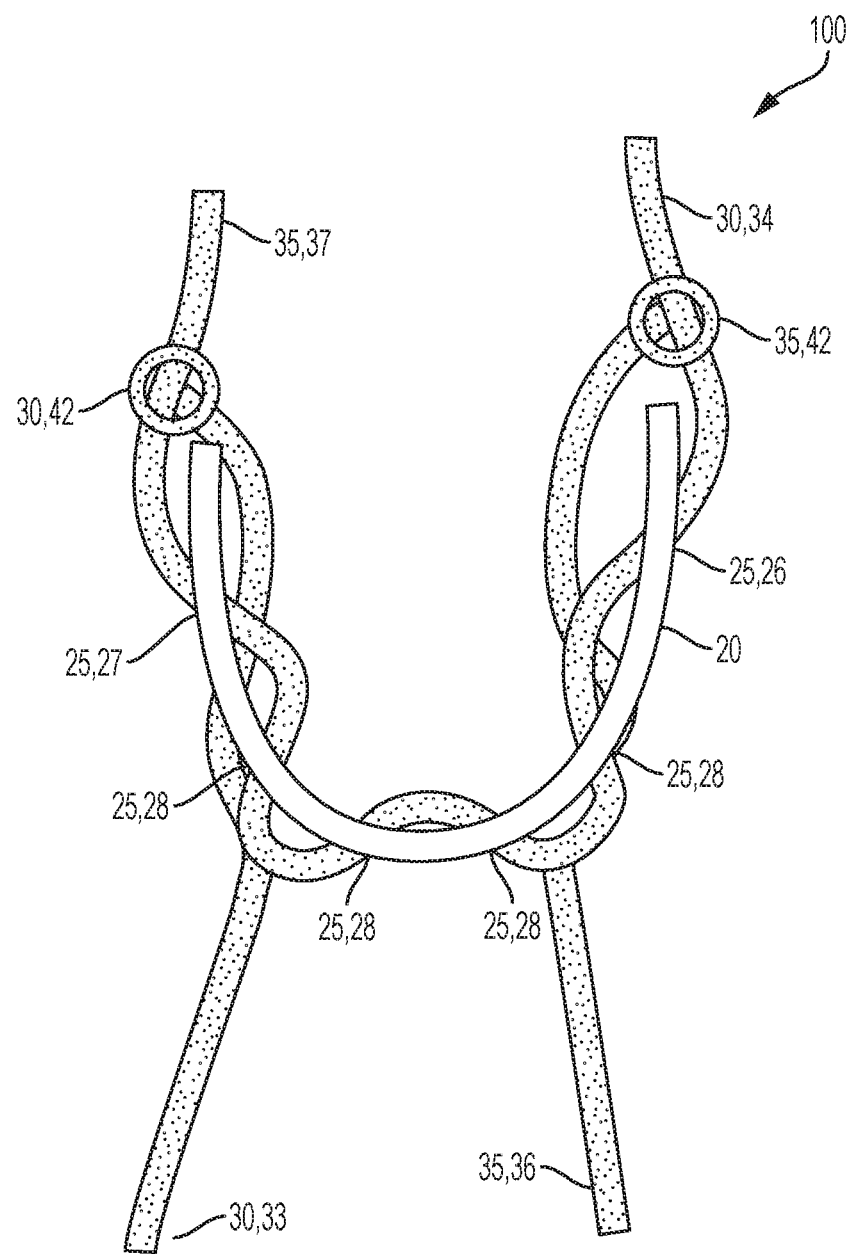
FIG. 12 represents a variation of the embodiment of FIG. 10.

FIG. 12 depicts a variation on the embodiment of FIGS. 10 and 11. As shown in FIG. 12, each of the standing ends 33, 36 are passed back though at least one loop (two shown in FIG. 12) formed between the filaments 30, 35 and the fibrous construct 20 between adjacent passing locations 25. This passing of the standing ends back through the loops helps to redirect, in an orderly fashion the direction of the standing ends 30, 35 such that they pass out of one end of a through hole while the working ends 34, 37 are directed to pass out of an opposite end of the through hole, an implementation of this anchor 100 being demonstrated in FIGS. 13-15.

Figure 13:
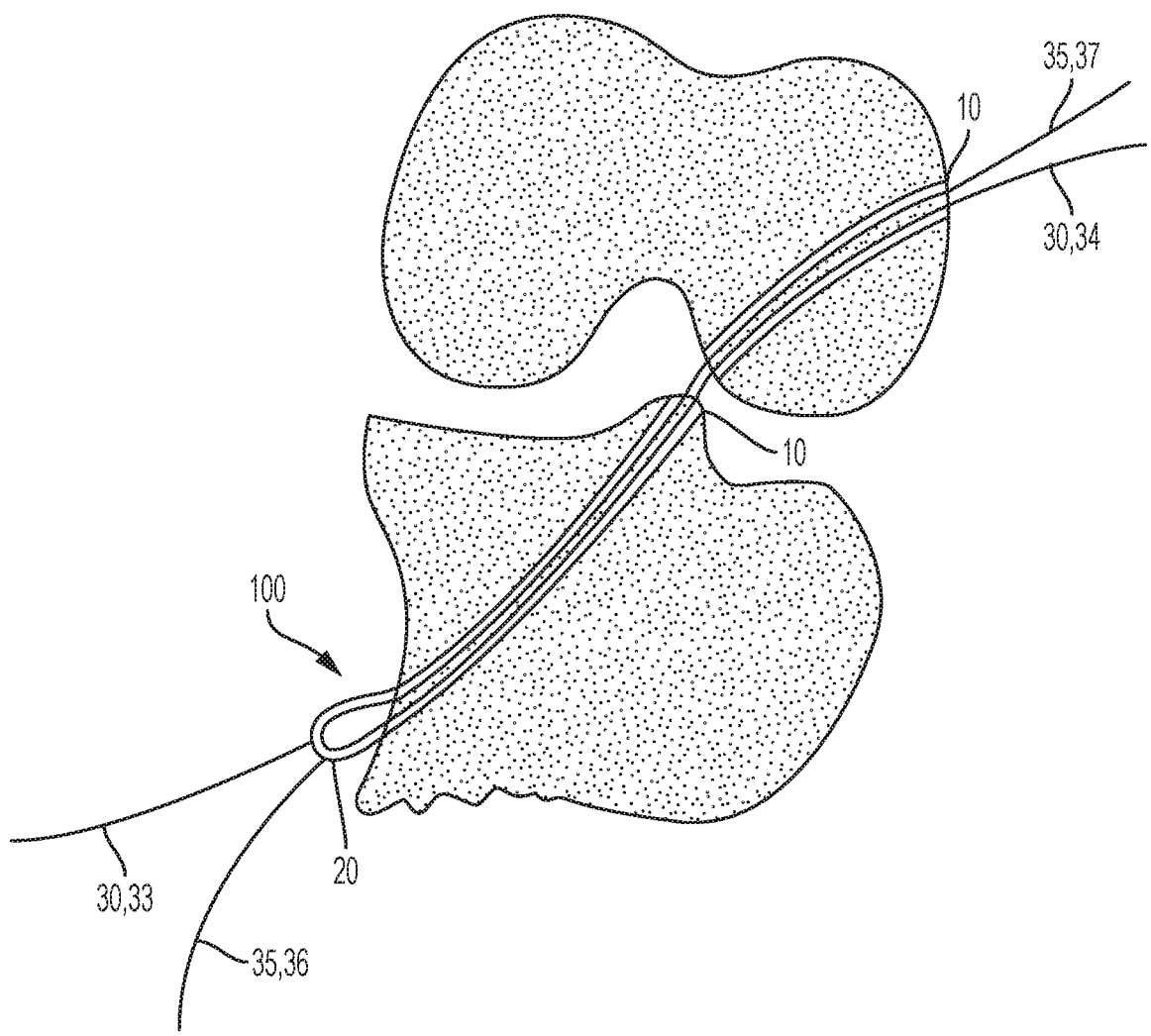
FIG. 13 represents the anchor of FIG. 12 at an initial step of installation in accordance with the present invention.

As shown in FIG. 13, the anchor 100 is positioned at one end of a hole 10 such that the fibrous construct 20 is pulled into a "U" shape. The working ends 34, 37 pass entirely through the hole 10 to extend there from while the standing ends 33, 36 remain exposed at the opposite end.

Figure 14:
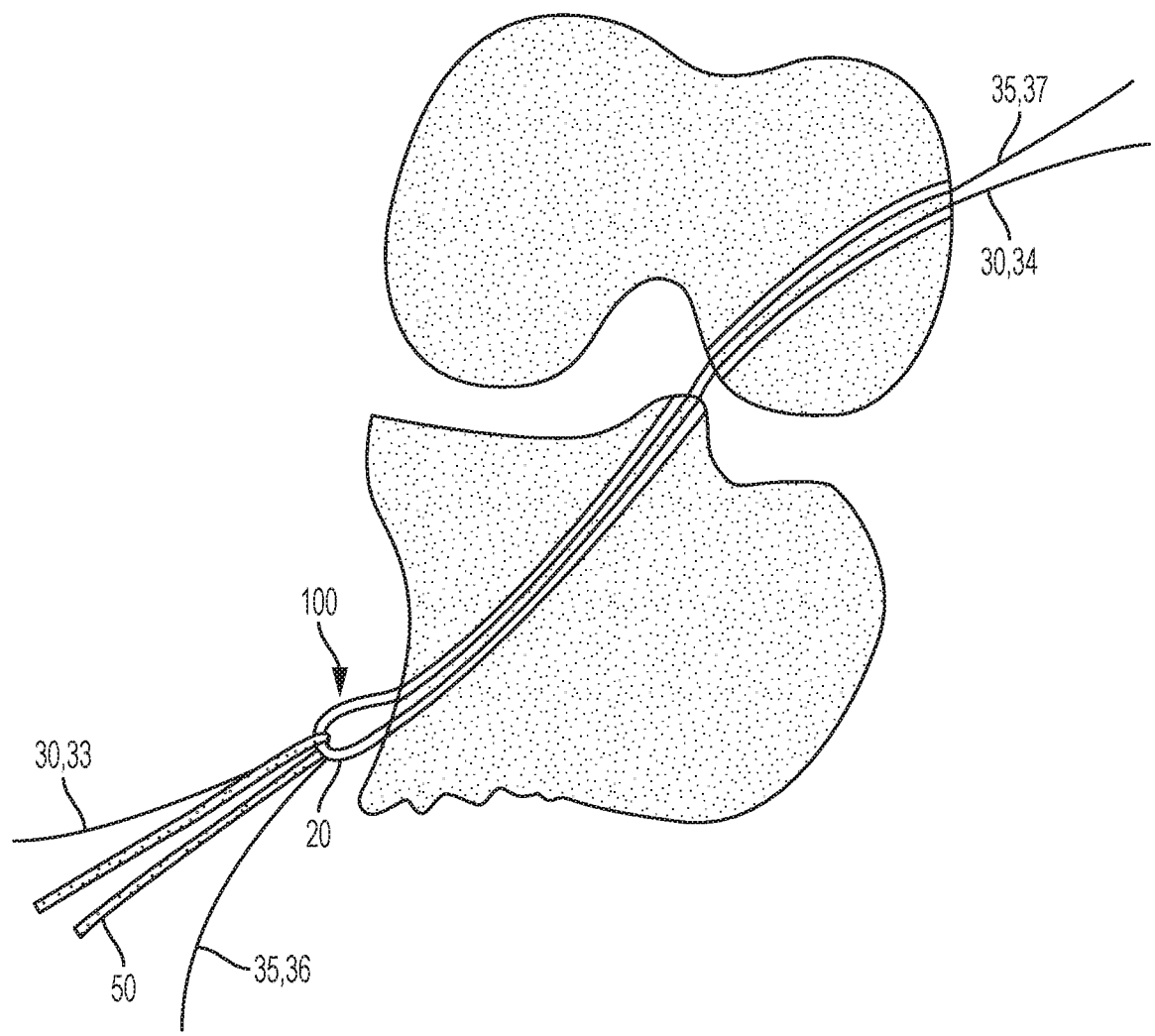
FIG. 14 represents an installation step subsequent to the step of FIG. 13.

In FIG. 14, a portion of connective tissue 50 (or other fibrous tissue) is passed through the "U" shaped fibrous construct 20 in the anchor 100 in preparation to be pulled through the hole 10.

Figure 15:
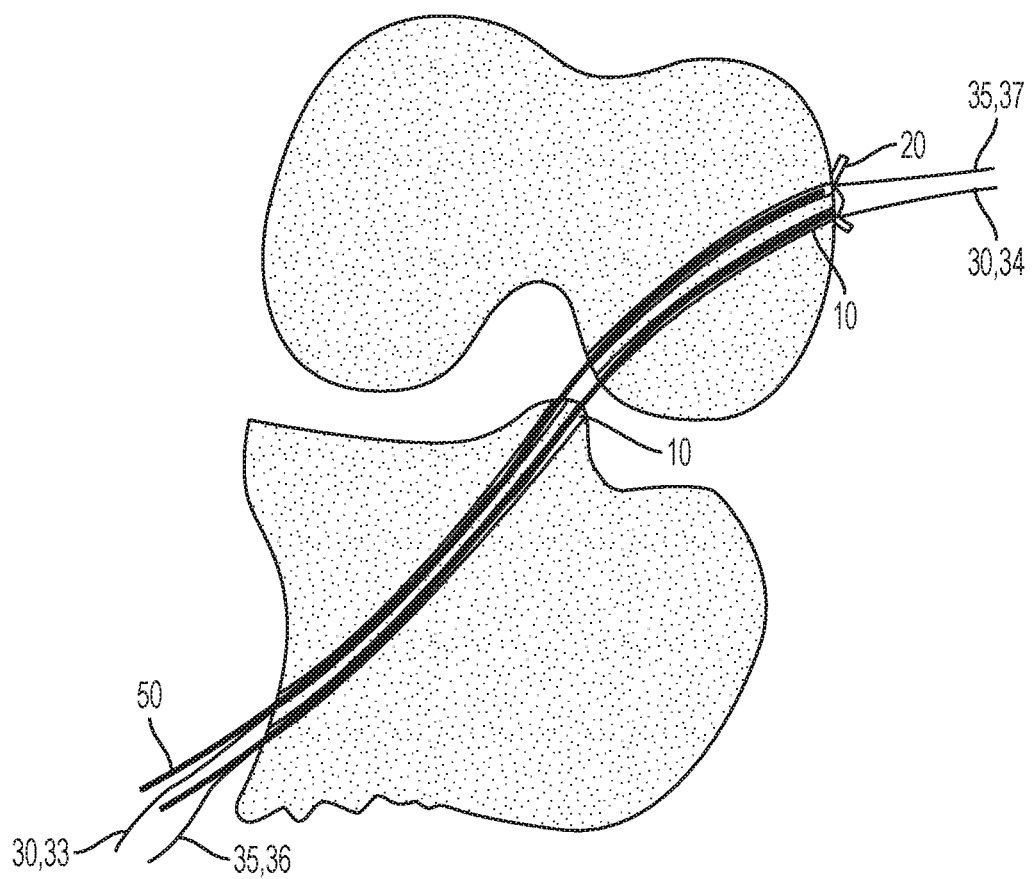
FIG. 15 represents an installation step subsequent to the step of FIG. 14.

In FIG. 15, the connective tissue 50 is drawn through the hole 10 by pulling on the working ends 34, 37 of the filaments 30, 35. Once the fibrous construct 20 is beyond the hole 10, the standing ends 33, 36 may be tensioned, causing the fibrous construct 20 to deploy into its second state in a manner similar to that of FIG. 11. Afterward the working ends 34, 37 and/or the standing ends 33, 36 may be tied, securing the connective tissue to the anchor 100 and the anchor 100 in its deployed, second state.

As with the previous embodiment, it may be helpful to color the individual ends of the filaments for differentiation during the surgical procedure.

All the embodiments and processes described above may be altered within the scope of the present invention to accommodate different size and strength requirements based on the variables provided above.

What is claimed is:
1. A method of anchoring tissue to bone, comprising the steps of:
   providing an anchor having an undeployed state and a deployed state, the anchor including:
   a flat fibrous construct having a first end and a second end, wherein:

in the undeployed state, the fibrous construct has a first fibrous construct width or thickness and a first fibrous construct length;

in the deployed state, the fibrous construct has a second fibrous construct width or thickness and a second fibrous construct length; and the second fibrous construct width or thickness being greater than the first fibrous construct width or thickness, the second fibrous construct length being shorter than the first fibrous construct length; and a filament having a first end and a second end passing through the fibrous construct in two locations including a first passing location nearest a first end of the fibrous construct, a second passing location nearest a second end of the fibrous construct, the filament remaining free to slide through the first passing location and the second passing location such that the filament can be removed from the flat fibrous construct from the first end of the fibrous construct and the second end of the fibrous construct;

inserting the anchor into a hole in a bone; and deploying the anchor into the hole.

2. The method of claim 1, wherein the flat fibrous construct comprises a lumen and wherein the fibrous construct is tubular.

3. The method of claim 1, wherein when the anchor is in the deployed state after the step of deploying:

the filament forms a semi-u-shape construct with an interior surface forming an interior space within a bone hole; and the first end and the second end of the flat fibrous construct is positioned within the interior space.

4. The method of claim 1, the filament having a longitudinal axis, the flat fibrous construct comprising:

a first state in which the flat fibrous construct is uncompressed and extends along the longitudinal axis of the filament; and a second state in which the flat fibrous construct is compressed and expanded in a direction perpendicular to longitudinal axis of the filament.

* * * * *